United States Patent [19]

Bryson

[11] Patent Number: 4,610,394
[45] Date of Patent: Sep. 9, 1986

[54] MOLDED DISPENSING CONTAINER

[75] Inventor: John D. Bryson, Milwaukee, Wis.

[73] Assignee: Vaportek, Inc., Milwaukee, Wis.

[21] Appl. No.: 245,396

[22] Filed: Mar. 19, 1981

[51] Int. Cl.[4] .............................................. A61L 9/12
[52] U.S. Cl. .................................... 239/57; 220/4 B; 239/59
[58] Field of Search .................................. 239/53–60; 220/4 B, 4 E, 339

[56] References Cited

U.S. PATENT DOCUMENTS

| | | | |
|---|---|---|---|
| 2,038,071 | 4/1936 | Wilhelm | 239/59 |
| 2,438,129 | 3/1948 | Rich | 239/59 |
| 2,578,827 | 12/1951 | Munnecke | 239/55 |
| 2,783,084 | 2/1957 | Paxton | 239/59 |
| 2,836,462 | 5/1958 | Wenner | 239/57 |
| 3,409,202 | 2/1966 | Belcher | 220/39 |
| 3,767,110 | 10/1973 | Congleton | 220/4 B |
| 3,817,371 | 6/1974 | Gatter | 239/57 |
| 4,244,470 | 1/1981 | Burnham | 220/4 B |

*Primary Examiner*—Andres Kashnikow
*Assistant Examiner*—Michael J. Forman
*Attorney, Agent, or Firm*—Michael, Best & Friedrich

[57] ABSTRACT

Disclosed herein is a container fabricated of plastic and including a tubular sidewall defining a hollow interior and having upper and lower margins, an elongated flat section having parallel side edges extending substantially between the upper and lower margins, and an arcuate section extending from and between the side edges of the flat section, together with upper and lower closure members extending in telescopic relation over the sidewall upper and lower margins and closing the upper and lower ends of the sidewall, which closure members are rotatable relative to the sidewall between arcuately spaced first and second positions, and valve means including respective apertures in the sidewall upper and lower margins and in the closure members, which apertures are substantially in register, and thereby open, when the closure members are in the first position and which apertures are substantially out of register, and thereby closed, when the closure members are in the second position.

Also disclosed herein is a blank for the sidewall, which blank includes a first flat portion having first and second spaced parallel edges, a first arcuate portion extending integrally from the first edge for arcuate movement relative to the flat portion about the first edge, and a second arcuate portion extending integrally from the second edge for arcuate movement relative to the flat portion about the second edge, which first and second arcuate portions have arcuate cross sections transversely of the first and second edges and have respective outer edges extending parallel to the first and second edges, which outer edges can be interfitted to establish the blank in a cylindrical form except for the flat portion.

13 Claims, 7 Drawing Figures

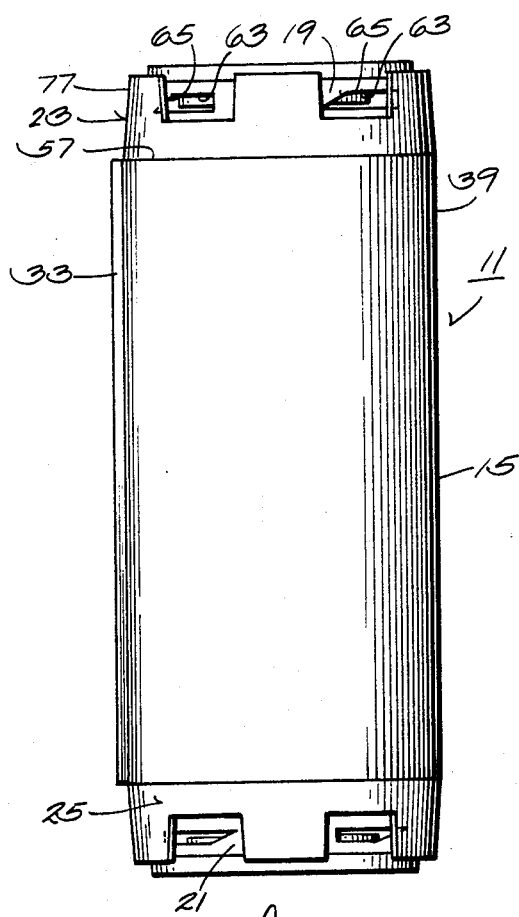
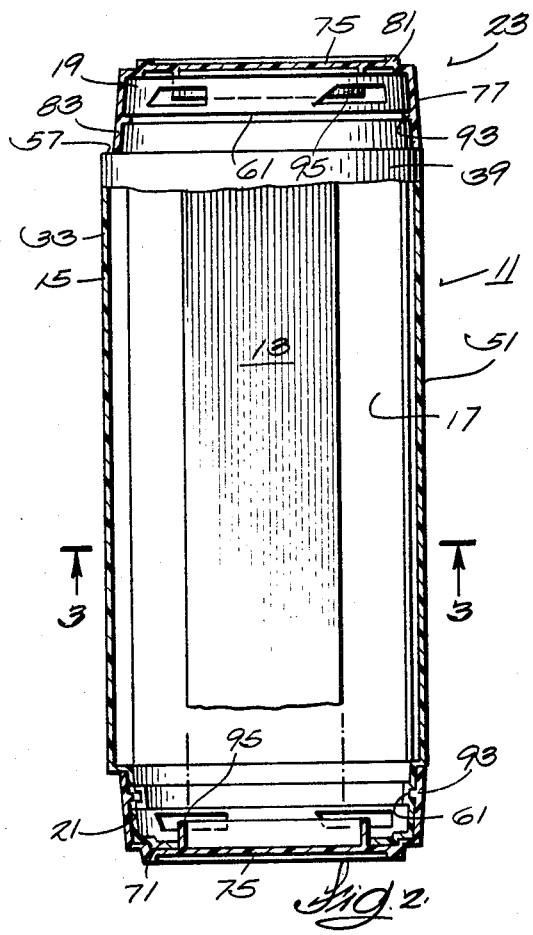
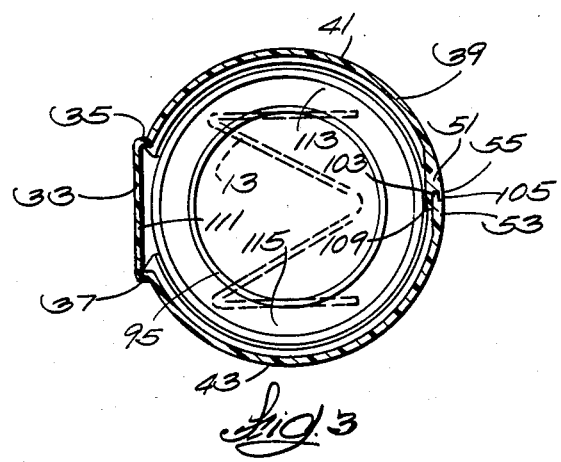

MOLDED DISPENSING CONTAINER

BACKGROUND OF THE INVENTION

The invention relates generally to valved devices or containers for dispensing into the atmosphere substances such as ordorants, deodorants, insecticides, perfumes, and the like. Attention is directed to the Watkins U.S. Pat. No. 3,785,556, issued Jan. 15, 1974, and to the Watkins U.S. Pat. No. 3,885,737, issued May 27, 1975, disclosing packages which contain substances to be dispensed and which are particularly adapted for use in the dispensing container disclosed herein.

Attention is also directed to the Wilhelm U.S. Pat. No. 2,038,071 issued Apr. 21, 1936, to the Thornton U.S. Pat. No. 3,790,081, issued Feb. 5, 1974, to the Watkins U.S. Pat. No. 3,923,934, issued Dec. 2, 1975, and to the Bryson U.S. Pat. No. 4,096,994, issued Apr. 17, 1978.

SUMMARY OF THE INVENTION

The invention provides a container which is fabricated of plastic and which includes a tubular sidewall defining a hollow interior and having upper and lower margins, an elongated flat section having parallel side edges extending substantially between the upper and lower margins, and an arcuate section extending from and between the side edges of the flat section, together with an upper closure member extending in telescopic relation over the sidewall upper margin and closing the upper end of the sidewall, which upper closure member is rotatable relative to the sidewall between arcuately spaced first and second positions, valve means including respective apertures in the sidewall upper margin and in the upper closure member, which apertures are substantially in register, and thereby open, when the upper closure member is in the first position, and which apertures are substantially out of register, and thereby closed, when the upper closure member is in the second position, a lower closure member extending in telescopic relation over the sidewall lower margin and closing the lower end of the sidewall, which lower closure member is rotatable relative to the sidewall between arcuately spaced first and second positions, and valve means including respective apertures in the lower margin and in the lower closure member, which apertures are substantially in register, and thereby open, when the lower closure member is in the first position and which apertures are substantially out of register, and thereby closed, when the lower closure member is in the second position.

The invention also provides a blank for a container sidewall, which blank is formed of plastic and comprises a first flat portion having first and second spaced parallel edges, a first arcuate portion extending integrally from the first edge for arcuate movement relative to the flat portion about the first edge, which first arcuate portion has an arcuate cross section transversely of said first edge and has a first outer edge extending parallel to the first edge, and a second arcuate portion extending integrally from the second edge for arcuate movement relative to the flat portion about the second edge, which second arcuate portion has an arcuate cross section transversely of the second edge and has a second outer edge extending parallel to the second edge for interfitting with the first outer edge to establish the blank in a cylindrical form except for the flat portion.

Other features and advantages of the embodiments of the invention will become known by reference to the following general description, claims and appended drawings.

IN THE DRAWINGS

FIG. 1 is a side elevation view of a container embodying various of the features of the invention.

FIG. 2 is a view similar to FIG. 1 with parts broken away and in section.

FIG. 3 is a sectional view taken along line 3—3 of FIG. 1.

Figure 5:
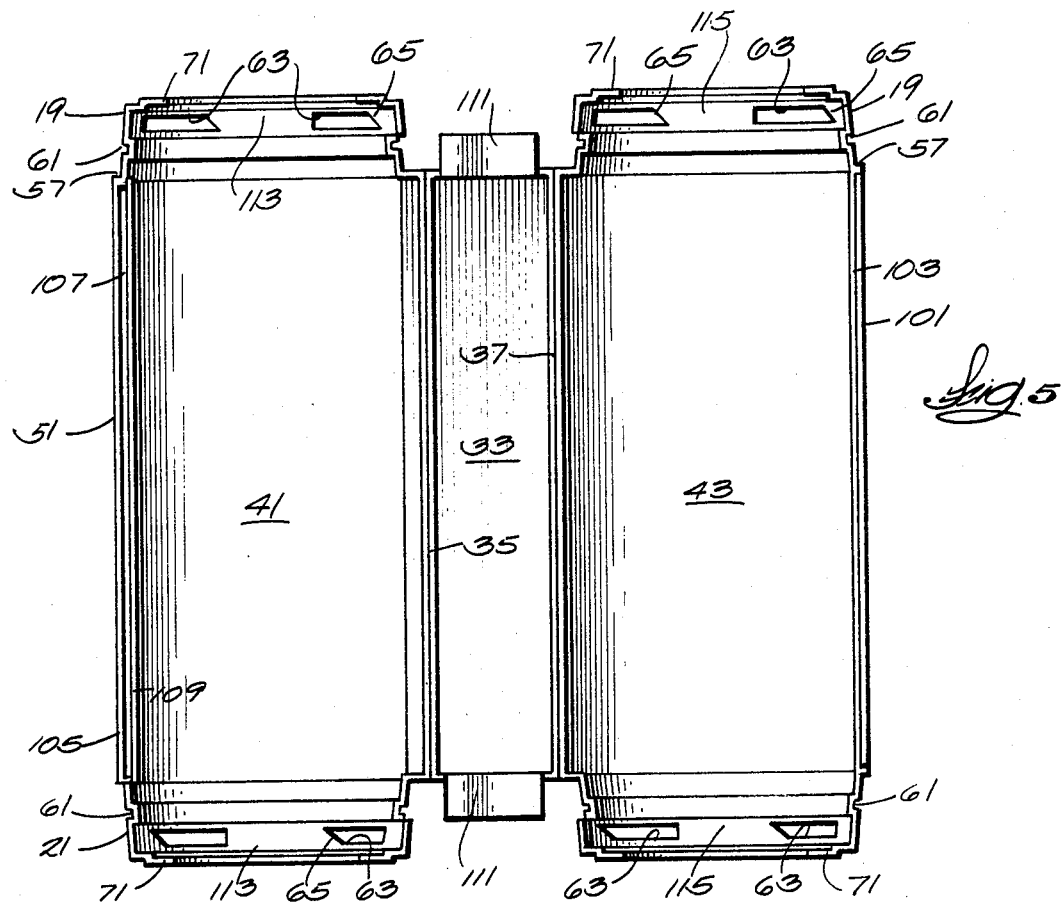
FIG. 5 is a plan view of the blank shown in FIG. 4.

Before explaining one embodiment of the invention in detail, it is to be understood that the invention is not limited in its application to the details of construction and the arrangement of components set forth in the following description or illustrated in the drawings. The invention is capable of other embodiments and of being practiced and carried out in various ways. Also, it is to be understood that the phraseology and terminology employed herein is for the purpose of description and should not be regarded as limiting.

GENERAL DESCRIPTION

Shown in FIGS. 1 and 2 is a container 11 for selectively dispensing substances such as ordorants, deodorants, insecticides and other like substances. The container shown in FIG. 1 encloses (See FIG. 2) a package 13 containing such a substance to be dispensed. One such package is disclosed in the Watkins U.S. Pat. No. 3,785,556 issued Jan. 15, 1974.

Figure 4:
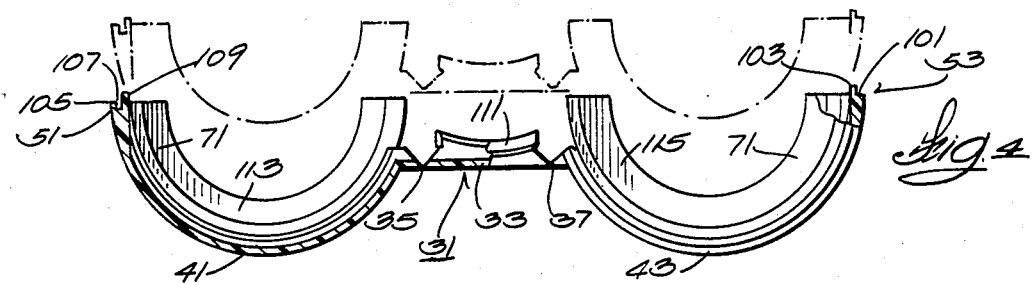
FIG. 4 is an end view of a blank from which a portion of the container shown in FIG. 1 is formed.

The container 11 is preferably fabricated of molded plastic parts or components formed of polypropolene and includes an endless sidewall 15 which defines a hollow interior 17 and which has upper and lower margins 19 and 21 defining open upper and lower ends. The container 11 also includes identically constructed upper and lower closure members 23 and 25 which are cup-shaped, which respectively telescopically assemble over the sidewall upper and lower margins 19 and 21 in closely fitting relation thereto, which are rotatable relative to the sidewall 15, and which, together with the sidewall 15, define upper and lower valve means providing selective access to, or closure of, the hollow interior 17 of the container 11. In FIG. 2, the upper closure member 23 is shown in cross-section and the upper margin 19, together with the upper portion of the exterior of the sidewall 15, are shown in elevation. Preferably, the sidewall 15 is fabricated (See FIGS. 4 and 5) from a blank 31 which can be extended in generally flat condition, as shown in FIGS. 4 and 5.

The sidewall 15 and upper and lower closure members 23 and 25 are fabricated such that, after assembly, the container 11 cannot be readily disassembled without rupture or breakage of one or more of the container components.

More particularly, the sidewall 15 includes (See FIG. 3) a flat section or portion 33 having opposed parallel side edges 35 and 37 which extend from and between the sidewall upper and lower margins 19 and 21. The sidewall 15 also includes an arcuate section 39 which extends from and between the side edges 35 and 37 of the flat section 33. The arcuate section 39 includes arcuate portions or sub-sections 41 and 43 which respectively extend from the side edges 35 and 37 of the flat section 33 and which respectively include outer edges 51 and 53 including means providing an interfitted seam 55 connecting together the outer edges 51 and 53 and providing the sidewall 15 with an endless configuration.

The sidewall upper and lower margins 19 and 21 are identically constructed and, accordingly, only the upper margin 19 will be disclosed in detail. In this regard, the upper margin 19 extends from the upper end of the flat section 33 and from the arcuate sub-sections 41 and 43 and, when the arcuate sub-sections 41 and 43 are assembled together, is preferably slightly conical in shape, and has, adjacent the flat section 33 and arcuate section 39, a diameter slightly inwardly spaced therefrom, thereby providing an annular shoulder 57.

Axially outwardly of the adjacent end of the sidewall sections 33 and 39, the upper margin includes an annular recess or groove 61. Axially beyond the annular recess 61, the upper margin includes one or more equi-angularly spaced apertures 63, four in the disclosed construction, which apertures 63 are preferably defined, in part, by an inclined edge 65 so as to afford fine control of the extent to which the apertures 63 can be opened and closed, as will be apparent hereinafter.

At the extreme axially outer end, the upper margin 19 includes a radially inwardly extending flange 71.

Figure 6:
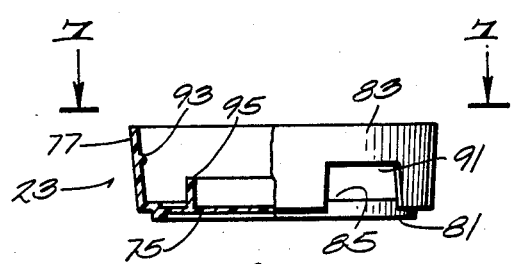
FIG. 6 is an elevational view, partially broken away and in section, of one of the closure members incorporated in the container shown in FIG. 1.
Figure 7:
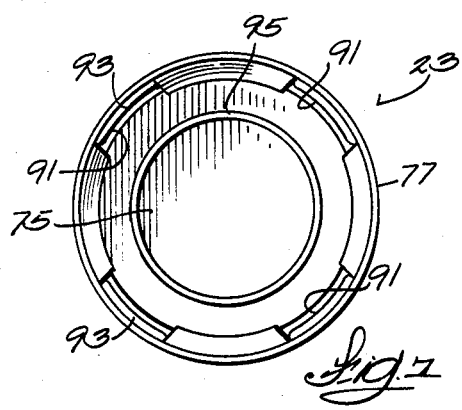
FIG. 7 is a view taken along line 7—7 of FIG. 6.

The upper and lower closure members 23 an 25 are also identically constructed and accordingly, only the upper closure member 23 will be described in detail. The upper closure member or cap 23 includes (See also FIGS. 6 and 7) an imperforate end wall 75, together with an annular wall 77 which is generally conical in shape, which closely interfits with the conical sidewall upper margin 19, and which includes an axially outer smaller segment 81 and an axially inner larger segment 83 which are offset with respect to one another. More particularly, the axially outer or smaller segment 81 extends from slightly outwardly beyond the end wall 75 and has a lower edge 85 located, (when assembled with the sidewall 15) adjacent to the upper margin flange 71. The lower edge 85 has a diameter slightly greater than the outer diameter of the uppermost end of the upper margin 19. The axially inner or larger segment 83 extends from slightly above the lower edge 85 of the axially outer segment 81 to adjacent the shoulder 59 between the sidewall upper margin 19 and the sidewall sections 33 and 39 so as to provide a smooth transition between the upper closure member 23 and the sidewall 15. The axially inner or larger segment 83 is provided with a series of openings or cut-outs 91 equal in number to the apertures 63 in the upper margin 19. The openings 91 are formed as interruptions along the axially outer edge of the larger or axially inner segment 83 of the upper closure member 23. The openings 91 have an arcuate length permitting full exposure of the apertures 63 in the sidewall upper margin 19 and are spaced such that the upper margin apertures 63 can be completely closed or located in underlying registry with the non-apertured portions of the axially inner segment 83 of the closure member 23.

Provided on the inner surface of the axially inner segment 83 of the closure member 23 is an inwardly projecting annular rib or projection 93 which snap fits relatively snuggly into the annular recess 61 in the sidewall upper margin 19, which is located so as to position the closure member end wall 75 in closely adjacent relation to the upper margin flange 71, and which permits rotation of the closure member 23 relative to the sidewall 15. The annular recess or groove 61 can either afford uninterrupted rotation of the closure member 23 relative to the sidewall 15 or can be fabricated so as to limit movement of the closure member 23 relative to the sidewall 15 to rotation of about 45° between a closed closure member position wherein the apertures 63 are fully out of registration with the openings 91 and an open closure member position wherein the apertures 63 are in full registry with the openings 91 to permit air flow into and out of the interior 17 of the container 11.

In order to space the ends of the package 13 located in the container 11 from the closure member end wall 75 so as to facillitate free circulation within the container, the closure member 23 also includes an annular rib or ring 95 which extends axially inwardly from the end wall 75 in radially inward relation from the annular wall 77 and, when assembled with the sidewall 15, in adjacently inward relation from the inward extent of the upper margin flange 71.

It is noted that when the annular rib 93 is received in the annular recess 61, the interfitting relation of the closure member to the sidewall 15 and of the arcuate sub-sections 41 and 43 is self locking and dis-assembly of the closure member 23 from the sidewall 15 and opening of the sidewall 15 is prevented in absence of the rupture of one of the components.

When the bottom or lower closure 25 is assembled to the bottom or lower margin 21 of the sidewall 15, the sidewall 15 is additionally locked in tubular configuration and the bottom or lower closure 25 cannot be removed from the lower margin 21 of the sidewall 15 without rupture of either the bottom closure member 25 or the sidewall 15.

It is also noted that the closure members 23 and 25, when not assembled to the sidewall 15, are readily stackable so as to reduce storage space.

Because the sidewall 15 is initially molded or fabricated in the generally flat blank 31 which is shown in FIGS. 4 and 5, the sidewalls 15, when not assembled in tubular form, can be readily stacked to reduce storage space.

More particularly, the numbers which have been applied to the various components of the sidewall 15 illustrated in FIGS. 1 and 2 have also been applied to the sidewall blank 31 shown in FIGS. 4 and 5.

It is noted that the side edges 35 and 37 of the sidewall flat section or portion 33 constitute both integral connections between the flat section 33 and the connected arcuate sub-sections or portions 41 and 43, as well as provide fold lines about which the arcuate sub-sections 41 and 43 are hinged for arcuate movement relative to the sidewall flat section 15.

It is further noted that the outer edges 51 and 53 of the side wall sub-sections 41 and 43 provide means which interfit when the blank 33 is formed in tubular configuration to provide a substantially air tight seal. More specifically, the outer edge 53 of the arcuate sidewall sub-section 43 includes, adjacent the outer surface of the blank 31, an outer edge portion 101 and, adjacent the inner surface of the blank 31, a tang 103 extending beyond the edge portion 101. The outer edge 51 of the arcuate sidewall sub-section 41 includes, adjacent the outer surface of the blank 31, an edge portion which, when the sub-sections 41 and 43 are interconnected, abuts the edge portion 101, a recess 107 which receives the tang 103, and, adjacent the inner surfaces of the blank 31, a tang 109 which, when the outer edges 51 and 53 are interfitted, extends beyond the mating line between the edge portions 101 and 105 and overlaps the inner surface of the arcuate sub-section 43.

It is futher noted that, in the blank 31, the upper and lower margins 19 and 21 are segmented, i.e., the upper margin 19 includes a central or minor segment 111 which extends from the flat sidewall portion 33 and major segments 113 and 115 which extend respectively from the arcuate sidewall sub-sections 41 and 43.

It is further noted that when the arcuate sub-sections 41 and 43 are moved to form the blank 31 into a tubular configuration, the minor or central upper margin segment 111 and the major upper margin segments 113 and 115 abut one another to provide a substantially continuous configuration.

The disclosed construction provides a container 11 which is fabricated from the sidewall blank 31 and two identical end closures 23 and 25, which, when assembled, is self-locking and cannot be disassembled without rupturing one or more of the components, which, when assembled, can be manipulated to selectively open and close the container interior 17, to thereby permit and prevent dispersal of the substance contained in the package 13, and which, when the closure members 23 and 25 are in closed position, provide a substantially air tight container.

It is further noted that the components, when not assembled, are readily stackable to reduce storage space and that the components can be readily assembled to provide the container 11 and to enclose the package 13 containing the substance to be dispensed.

It is also noted that the sidewall flat section 33 facilitates attachment of the container 11 to walls and application to the container 11 of identifying indicia.

Various of the features of the invention are set forth in the following claims.

I claim:

1. A container fabricated of plastic and including a sidewall defining a hollow interior and having spaced end margins defining sidewall ends, one of said end margins including an inwardly extending flange, said sidewall also having a side portion extending intermediate said end margins and including first and second sub-sections which have respective outer edges including interfitting edge means defining a substantially air-tight side seam, a closure member extending in a telescopic relation over one of said sidewall end margins and closing the adjacent one of said sidewall ends, said closure member being rotatable relative to said sidewall between arcuately spaced first and second positions, including an end wall located adjacent said flange, and a ring structure extending inwardly of said container from said end wall and from adjacent said flange valve means including respective apertures in said one end margin and in said closure member, said apertures being substantially in register, and thereby open, when said closure member is in said first position and said apertures being substantially out of register, and thereby closed, when said closure member is in said second position, interfitting means on said one end margin and on said closure member for permitting relative rotation therebetween, for preventing disassembly therebetween, and for preventing disassembly of said edge means, and an end member extending in telescopic relation to the other of said end margins of said sidewall and closing the other of said sidewall ends.

2. A container fabricated of plastic and including a sidewall defining a hollow interior and having spaced end margins, an elongated flat section having parallel side edges extending substantially between said end margins, and an arcuate section extending from and between said side edges of said flat section to define, inwardly of said end margins, a body which is generally cylindrical except for said flat section, said arcuate section including first and second sub-sections which respectively integrally extend from said parallel side edges and have respective outer edges including interfitting edge means defining a substantially air-tight side seam, a first closure member extending in telescopic relation over one of said sidewall end margins and closing the adjacent end of said sidewall, said first closure member being rotatable relative to said sidewall between arcuately spaced first and second positions, valve means including respective apertures in said one margin and in said first closure member, said apertures being substantially in register, and thereby open, when said first closure member is in said first position and said apertures being substantially out of register, and thereby closed, when said first closure member is in said second position, interfitting means on said one end margin and on said first closure member for permitting relative rotation therebetween, for preventing disassembly therebetween, and for prevent disassembly of said edge means and, a second closure member extending in telescopic relation to said other of said end margins of said sidewall and closing the other end of said sidewall.

3. A container in accordance with claim 2 and further including a package of the substance to be dispensed within said hollow interior, and wherein one of said closure members includes an end wall, and means extending inwardly of said container from said end wall for spacing said package from said end wall.

4. A container in accordance with claim 2 wherein said closure members are identically constructed.

5. A container in accordance with claim 3 wherein said closure members are fabricated of plastic and are generally of cup shape, each including an end wall and a conical annular wall extending from said end wall and including said apertures.

6. A container in accordance with claim 2 wherein said interfitting means on said one end margin and on said first closure member comprises a recess in one of said one end margin and said first closure member and a rib which can be snap fitted into said recess on the other of said one end margin and said first closure member.

7. A container in accordance with claim 2 wherein said first closure member includes an end wall, and a ring structure extending inwardly of said container from said end wall, and wherein said one end margin includes an inwardly extending flange located adjacent to said end wall and extending to adjacent said ring structure.

8. A container fabricated of plastic and including a sidewall defining a hollow interior and having spaced first end second end margins, an elongated flat section having parallel side edges extending substantially between said end margins, and an arcuate section extending from and between said side edges of said flat section to define, inwardly of said end margins, a body which is generally cylindrical except for said flat section, said arcuate section including first and second sub-sections which respectively integrally extend from said parallel side edges and have respective outer edges including interfitting edge means defining a substantially air-tight side seam, a first closure member extending in telescopic relation over said first sidewall end margin and closing the adjacent end of said sidewall, said first closure member being rotatable relative to said sidewall between arcuately spaced first and second positions, first valve means including respective first apertures in said first end margin and in said first closure member, said first apertures being substantially in register, and thereby open, when said first closure member is in said first position and said first apertures being substantially out of register, and thereby closed, when said first closure member is in said second position, first interfitting means on said first end margin and on said first closure member for permitting relative rotation therebetween, for preventing disassembly therebetween, and for preventing disassembly of said edge means, a second closure member extending in telescopic relation to said second sidewall end margin and closing the other end of said sidewall, said second closure member being rotatable relative to said sidewall between arcuately spaced first and second positions, second valve means including respective second apertures in said second end margin and in said second closure member, said second apertures being substantially in register, and thereby open, when said second closure member is in said first position and said second apertures being substantially out of register, and thereby closed, when said second closure member is in said second position, and second interfitting means on said second end margin and on said second closure member for permitting relative rotation therebewteen a for preventing disassembly therebetween, and for preventing disassembly of said edge means.

9. A container in accordance with claim 8 and further including a package of the substance to be dispensed within said hollow interior, and wherein one of said closure members includes an end wall, and means extending inwardly of said container from said end wall for spacing said package from said end wall.

10. A container in accordance with claim 8 wherein said closure members are identically constructed.

11. A container in accordance with claim 8 wherein said closure members are fabricated of plastic and are generally of cup shape, each including an end wall and a conical annular wall extending from said end wall and including said apertures.

12. A container in accordance with claim 8 wherein said first and second interfitting means each respectively comprises a recess in one of said margin and said closure member and a rib which can be snap fitted into said recess on the other of said margin and said closure member.

13. A container in accordance with claim 8 wherein one of said closure members includes an end wall, and a ring structure extending inwardly of said container from said end wall, and wherein one of said end margins includes an inwardly extending flange located adjacent to said end wall and extending to adjacent said ring structure.

* * * * *